(12) United States Patent
Huebner et al.

(10) Patent No.: US 7,927,332 B2
(45) Date of Patent: Apr. 19, 2011

(54) BONE REAMER

(75) Inventors: Randall J. Huebner, Beaverton, OR (US); Steven P. Horst, Dayton, OR (US)

(73) Assignee: Acumed LLC, Hillsboro, OR (US)

( * ) Notice: Subject to any disclaimer, the term of this patent is extended or adjusted under 35 U.S.C. 154(b) by 729 days.

(21) Appl. No.: 11/274,597

(22) Filed: Nov. 14, 2005

(65) Prior Publication Data

US 2006/0106393 A1 May 18, 2006

Related U.S. Application Data

(60) Provisional application No. 60/627,721, filed on Nov. 12, 2004.

(51) Int. Cl.
*A61B 17/16* (2006.01)
(52) U.S. Cl. .......................... 606/80; 606/62
(58) Field of Classification Search .................. 606/80, 606/79, 86 R, 62–68, 170; 408/201, 80, 408/82
See application file for complete search history.

(56) References Cited

U.S. PATENT DOCUMENTS

| | | | | |
|---|---|---|---|---|
| 2,786,218 A * | 3/1957 | Yousem | ...................... | 15/104.33 |
| 4,466,429 A * | 8/1984 | Loscher et al. | ............... | 606/180 |
| 4,541,423 A * | 9/1985 | Barber | ............................. | 606/80 |
| 4,706,659 A * | 11/1987 | Matthews et al. | ............... | 606/80 |
| 4,751,922 A * | 6/1988 | DiPietropolo | .................. | 606/80 |
| 4,978,350 A | 12/1990 | Wagenknecht | | |
| 5,049,150 A | 9/1991 | Cozad | | |
| 5,122,134 A * | 6/1992 | Borzone et al. | ................. | 606/80 |
| 5,342,363 A * | 8/1994 | Richelsoph | ..................... | 606/79 |
| 5,464,406 A * | 11/1995 | Ritter et al. | .................. | 606/86 R |
| 5,527,316 A * | 6/1996 | Stone et al. | ..................... | 606/80 |
| 5,540,694 A * | 7/1996 | DeCarlo et al. | ................. | 606/80 |
| 5,562,673 A * | 10/1996 | Koblish et al. | .................. | 606/80 |
| 5,573,537 A | 11/1996 | Rogozinski | | |
| 5,591,170 A * | 1/1997 | Spievack et al. | ................ | 606/82 |
| 5,645,545 A * | 7/1997 | Bryant | ............................ | 606/62 |
| 5,693,047 A | 12/1997 | Meyers et al. | | |
| 5,697,930 A * | 12/1997 | Itoman et al. | ................... | 606/62 |
| 5,855,581 A | 1/1999 | Koblish et al. | | |
| 5,891,148 A | 4/1999 | Deckner | | |
| 5,908,423 A * | 6/1999 | Kashuba et al. | ................ | 606/80 |
| 5,931,841 A * | 8/1999 | Ralph | ............................. | 606/85 |
| 6,004,321 A * | 12/1999 | Graser | ............................ | 606/53 |
| 6,033,407 A * | 3/2000 | Behrens | ......................... | 606/62 |
| 6,197,031 B1 | 3/2001 | Barrette et al. | | |
| 6,517,581 B2 | 2/2003 | Blamey | | |
| 7,491,203 B2 * | 2/2009 | Harris et al. | ..................... | 606/80 |
| 2006/0184174 A1 * | 8/2006 | Harris et al. | ..................... | 606/80 |
| 2010/0217267 A1 * | 8/2010 | Bergin et al. | .................... | 606/80 |
| 2011/0015634 A1 * | 1/2011 | Smith et al. | ...................... | 606/80 |

* cited by examiner

*Primary Examiner* — Eduardo C Robert
*Assistant Examiner* — Jan Christopher Merene
(74) *Attorney, Agent, or Firm* — Kolisch Hartwell, PC

(57) ABSTRACT

Systems, including apparatus, methods, and kits, for reaming bones with bone reamers.

10 Claims, 2 Drawing Sheets

BONE REAMER

CROSS-REFERENCE TO PRIORITY APPLICATION

This application is based upon and claims the benefit under 35 U.S.C. §119(e) of the following U.S. provisional patent application, which is incorporated herein by reference in its entirety for all purposes: Ser. No. 60/627,721, filed Nov. 12, 2004.

BACKGROUND

The human skeleton is composed of 206 bones that perform a variety of important functions, including support, movement, protection, storage of minerals, and formation of blood cells, among others. Among these bones, the long bones (e.g., the femur, tibia, and fibula of the legs; and the humerus, radius, and ulna of the arms, among others) provide structural limb support and enable movement and locomotion. To ensure that the long bones retain their ability to perform these functions, and to reduce pain and disfigurement, long bones that are fractured or otherwise compromised should be repaired promptly and properly.

Fractured bones typically are treated using fixation devices. These devices reinforce the bone around the fracture and keep the bone aligned during healing. Fixation devices may take a variety of forms, including casts for external fixation, and bone plates, bone screws, wires, and/or rods for internal fixation. For example, to treat a more severely fractured long bone, it may be necessary or desirable to fix fragments of the bone using an intramedullary rod received in the medullary canal of the bone to stabilize the fragments.

The installation of an intramedullary rod in a fractured long bone generally involves enlargement of the bone's medullary canal with a reamer so that the rod fits into the canal. A standard procedure involves use of a guide wire, as follows. First, an entry hole that communicates with the medullary canal of the long bone may be formed near an end of the long bone. Second, a guide wire may be inserted through the entry hole and into the canal, so that the guide wire extends along the length of the canal. Third, a cannulated reamer (a "wire-guided" reamer) then may be placed over the guide wire, allowing the reamer to slide along the guide wire as the reamer widens regions of the medullary canal. Finally, after reaming is completed, a suitable intramedullary rod may be inserted into the widened canal and secured to the bone (e.g., using bone screws).

Wire-guided bone reamers may have several disadvantages. For example, wire-guided reamers may be difficult to clean and sterilize. In addition, these reamers must have a shaft diameter substantially greater than that of the guide wire, leaving less room around the shaft in the reamed canal for bone debris to accumulate. Consequently, bone debris may be packed ahead of these reamers as they ream bone, resulting in increased pressure, which may damage bone and/or create embolisms that obstruct blood flow. Additional disadvantages of wire-guided reamers involve the use of a guide wire. In particular, the guide wire, to be received by wire-guided reamers, should be thin. A guide wire that is thin may be challenging to feed past fracture sites and may be too flexible to aid in fracture reduction. Furthermore, insertion (and optional retrieval) of any guide wire increases surgical time during installation of an intramedullary rod.

SUMMARY

The present teachings provide systems, including apparatus, methods, and kits, for reaming bones with bone reamers.

DETAILED DESCRIPTION

The present teachings provide systems, including apparatus, methods, and kits, for reaming bones with bone reamers. The reamers may be self-guided, that is, configured to be used in a medullary canal without guide wires. The self-guided reamers of the present teachings thus may provide a number of advantages over wire-guided reamers, including easier cleaning, simplified installation of intramedullary rods (and thus reduced time in surgery), and/or improved fracture reduction, among others.

Figure 1:
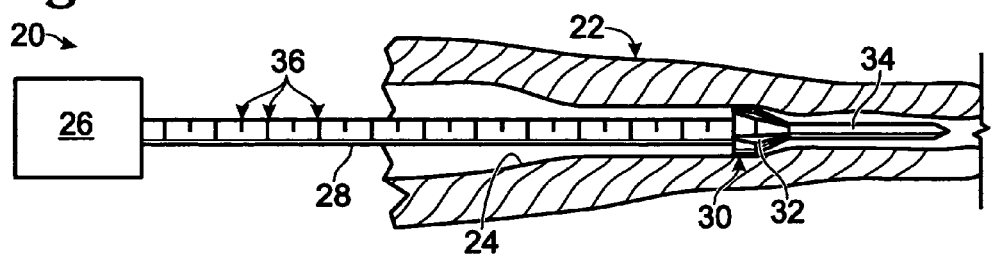
FIG. 1 is a somewhat schematic, partially sectional view of an exemplary bone reamer widening the medullary canal of a bone, in accordance with aspects of the present teachings.

FIG. 1 shows a somewhat schematic representation of an exemplary bone reamer 20 constructed in accordance with the present teachings and shown reaming a bone 22 by widening the medullary canal 24 of the bone. Reamer 20 may include a driver-engagement structure 26 for coupling torque from a driver to the reamer so that the reamer turns in relation to bone. Reamer 20 also may include a shaft 28, a cutting head 30 with flutes 32, and a tip 34, among others, with these structures arrayed proximally to distally from the driver-engagement structure, generally in a fixed (or fixable) relative disposition.

The shaft may have any suitable structure, for example, being elongate, flexible, and/or noncannulated. In some examples, the shaft may include indicia 36, such as marks and/or alphanumeric characters positioned to indicate the depth of the reamer in bone. Furthermore, the shaft may have a diameter smaller than the shaft of wire-guided reamers, to provide a greater space between the shaft and the wall of the medullary canal for accumulation of bone debris produced by the cutting head.

The cutting head generally performs the primary cutting and/or excavation functions of the reamer. Accordingly, the diameter of the cutting head may determine the diameter of the channel reamed in the bone.

The tip may have any suitable structure, for example, being elongate and extending distally from the cutting head, to guide the cutting head along a medullary canal without the need of a separate guide wire. In some examples, the diameter and/or stiffness of the tip may be greater than that of standard guide wires, to provide a stiffer, more useful guide. However, the tip also may be flexible enough to guide the reamer along a nonlinear path through portions of the canal that bend.

These and other aspects of the present teachings are described below, including, among others, (I) overview of reamers, including (A) driver-engagement structures, (B) shafts, (C) cutting heads, (D) tips, and (E) compositions; (II) methods of making reamers; (III) methods of using reamers; (IV) kits; and (V) an exemplary reamer.

I. Overview of Reamers

A reamer, as used herein, is any device configured to widen a cavity in bone by cutting the bone adjacent the cavity. The reamer may be configured to widen any suitable bone cavity, including a medullary canal (unreamed or previously reamed), a drilled or punched hole in bone (e.g., an entry hole into a medullary canal, among others), and/or the like. Furthermore, the reamer may be configured to widen any suitable portion of the cavity including a portion or all of the length of the canal. In some examples, the reamer may widen a narrowed portion of the cavity selectively, such as an isthmus of a medullary canal. The reamer may be configured to cut using rotary and/or axial motion.

Further aspects of reamers are included in the following sub-sections, including, (A) driver-engagement structures, (B) shafts, (C) cutting heads, (D) tips, and (E) compositions.

I.A Driver-Engagement Structures

A reamer may include a driver-engagement structure or base through which the reamer may be coupled to a driver. The driver-engagement structure may be configured to be grasped by hand, for operating the reamer manually. The driver-engagement structure thus may include a transverse bar and/or a knurled surface geometry, among others, to facilitate direct hand operation. Alternatively, or in addition, the driver-engagement structure may be configured to be coupled to a manually-driven and/or power-driven driver. The driver-engagement structure thus may be configured to be engaged by and mounted to a chuck and/or collet, among others.

The driver-engagement structure may have any suitable disposition in the reamer. Generally, the driver-engagement structure may be disposed near or at the proximal end of the reamer, and secured to the shaft. In some examples, the driver-engagement structure may be provided by the shaft itself. In any case, this structure may be configured to establish a connection with a driver, and to maintain a connection to the driver when the reamer is inserted a desired distance into the medullary canal.

I.B Shafts

A reamer may include a shaft joining the driver-engagement structure to a cutting head. The shaft may be noncannulated (solid), that is, lacking an axial bore that extends along the entire length of the shaft, or the shaft may be cannulated (formed as a tube with an axial bore), for example, to permit a guide wire to be received in the bore. If cannulated, the bore of the shaft may communicate with bores disposed adjacent the shaft, for example, in the driver-engagement structure, cutting head, and/or tip. Accordingly, the reamer may be cannulated along all, a portion of, or none of its length.

The shaft may have any suitable shape. The shaft may be elongate, with a linear geometry overall. Locally within the shaft, the shaft may be linear or nonlinear, for example, having a coiled (helical) geometry, as in a coiled spring. The shaft may have any suitable cross-sectional configuration, including circular, elliptical, oval, polygonal (such as square, hexagonal, etc.), rosette, and/or the like. The cross-sectional configuration may be constant or may vary along the length of the shaft. The surface of the shaft may be smoothly contoured or may include ridges/grooves that extend along and/or around the shaft.

The shaft may have any suitable length and diameter (or width). The length of the shaft may represent a substantial portion of the overall length of the reamer. Accordingly, the shaft may be longer than a region of bone along which the cutting head is placed (for example, to permit the driver-engagement structure and driver to remain exterior to the bone during reaming), and thus may be configured according to the intended use of the reamer. For example, the shaft may be longer for longer bones and/or for narrowed canal regions spaced farther from an entry end of a bone. Exemplary lengths of the shaft correspond generally to the at least about one-half or at least about two-thirds the length of a target bone, such as ulna or tibia, or about 10-60 cm, among others. The diameter of the shaft may be less than the diameter of the cutting head, or about 2-10 mm, among others. The diameter may be constant along the length of the shaft or may vary, for example, tapering toward the cutting head and/or driver-engagement structure.

The shaft may be flexible or rigid. A flexible shaft, as used herein, refers generally to an ability of the shaft to be bent significantly in response to the stresses exerted on the shaft during a typical reaming procedure. The shaft is generally configured to bend reversibly, so that the shaft returns to its original shape after these stresses are removed, without significant functional modification of the shaft. Reversible bending may allow the reamer to be used more than once. Bending of the shaft may permit the cutting head to follow a nonlinear path along a medullary canal, so that bone is not removed and/or damaged unnecessarily. The shaft may be considered bent significantly, as used herein, if the shaft deviates from a linear configuration by at least about one, two, or five degrees, among others. The shaft also may not be overly flexible, so that torque can be transmitted through the shaft, from a driver to the cutting head, without excessively twisting the shaft. A suitable flexibility for the shaft may be achieved by forming the shaft of a material having an appropriate Young's modulus, and by selecting a suitable diameter for the shaft, among others. A noncannulated shaft generally may have a smaller diameter than a cannulated shaft and thus may be configured to be more flexible. In some embodiments, the shaft may be relatively rigid so that it is suitable for reaming along an exclusively linear path, such as for placement of a prosthesis having a rigid stem.

The shaft may include or be used with other features or accessories that facilitate its use. For example, the shaft may include visible indicia disposed on the exterior of the shaft. The indicia may include one or more length/depth marks to indicate how far the reamer has been introduced into bone, to avoid reaming too far into bone. The indicia also or alternatively may include alphanumeric characters, symbols, and/or colors, to identify length/depth positions along the shaft, to identify the size/type/use of the reamer, and/or the like. In some embodiments, the shaft may be coupled to a stop structure of increased diameter and configured to restrict excessive advancement of the reamer into bone. The stop structure may be permanently fixed on the shaft or may be adjustably positioned thereon.

I.C Cutting Heads

A reamer may include a cutting head configured to widen a cavity in bone by removing bone adjacent the cavity. The cutting head may be disposed at a fixed and/or adjustable position between the shaft and the tip. The cutting head may be noncannulated (solid), that is, lacking an axial bore that extends along the entire length of the cutting head, or the cutting head may be cannulated (having an axial bore), for example, to permit a guide wire to be received in the bore or to receive a portion of the shaft and/or tip, among others.

The cutting head may have any suitable shape. For example, the cutting head may be generally conical, cylindrical, bullet-shaped, ellipsoidal, egg-shaped, spherical, etc. The cutting head thus may be elongate or may be shorter as measured along the long axis of the reamer than the head's diameter measured transverse to this long axis. The cutting head may include cutting surfaces/edges configured to cut bone. The cutting surfaces/edges may be defined by one or more flutes formed as one or more recesses in the lateral surface of the cutting head. These flutes may extend over any suitable portion of the axial dimension of the cutting head, for example, extending between opposing ends of the cutting head or a portion thereof. In some examples, the flutes may define channels through which bone debris may pass to a space around the shaft during reaming, to reduce pressure build-up. The flute(s) may have any suitable disposition on the cutting head. For examples the flutes may be positioned at radially symmetrical positions around the central axis of the cutting head. Each flute may extend obliquely (and/or circumferentially/axially) on the cutting head, for example, in a generally helical path along the cutting head. Each flute may define a cutting edge at one edge of the flute (for cutting in one rotational direction of the cutting head) or both opposing edges of the flute (for cutting in both rotational directions of the cutting head). Each flute may have any suitable width and depth.

The cutting head may have any suitable length and diameter (or width). The length of the cutting head may be substantially less than the length of the shaft and/or tip. Thus, in some embodiments, the length of the cutting head may be no more than about one-fifth, one-third, or one-half the length of the shaft and/or the tip, among others. In the same and/or other embodiments, the length of the cutting head may be about 0.5-5 cm, among others. A shorter cutting head may be preferable because a shorter cutting head may be able to travel a nonlinear path more readily, and/or may minimize contact with the interior of the medullary canal, thereby reducing intramedullary pressure during reaming. The diameter of the cutting head (generally, the maximum diameter of the cutting head measured transverse to the long axis of the reamer) may be less than the diameter of the shaft and/or the tip. Thus, in some embodiments, the diameter of the cutting head may be at least about twice or three times the diameter of the shaft and/or tip. The diameter of the cutting head may vary along its length, for example, so that the cutting head tapers toward the tip and/or shaft. In the same and/or other embodiments, the diameter of the cutting head may be about 2-20 mm, among others.

I.D Tips

A reamer may include a tip configured to guide the cutting head into a cavity in bone. The tip may be disposed on the distal side of the cutting head, coaxial with the cutting head and shaft, and opposing the shaft. The tip may be disposed at a fixed and/or adjustable axial position relative to the shaft and the cutting head. The tip may be solid, that is, lacking a cavity that extends along some or all of length of the tip, or the cutting tip may be at least partially hollow, for example, cannulated to permit a guide wire to be received by the tip or to facilitate assembly with the cutting head and/or shaft, among others.

The tip may have any suitable shape. The tip may be elongate parallel to the long axis of the reamer. The tip thus may have a linear or nonlinear configuration. In some examples, the tip may be generally linear, but may be nonlinear (such as helical) locally. The tip may have any suitable cross-sectional configuration, including circular, elliptical, oval, and/or polygonal (square, hexagonal, etc.), and the cross-sectional configuration may be substantially constant or may vary. The tip may include any suitable end structure, such as a blunt (flat or rounded, among others) or pointed distal end (spaced from the cutting head). In some examples, the tip may include a cutting edge, for example, extending axially, helically, and/or transversely along the length of the tip or disposed near the distal end. Accordingly, the tip may be configured to form a hole or to follow a pre-formed hole or cavity, among others.

The tip may have any suitable length and diameter (or width). The length of the tip may be sufficient to span fracture sites in long bones. In some examples, the length of the tip may be substantially less than the length of the shaft. The length of the tip may be less than or more than the length of the cutting head. In some examples, the length may be about two, four, or eight times the length of the cutting head. The length of the tip similarly may be less than or more than the diameter of the cutting head. In some examples, the length of the tip may be at least about two, four, or eight times the diameter of the cutting head. Exemplary tip lengths include, but are not limited to, about 0.5-10 cm, among others. The diameter of the tip is less than the diameter of the cutting head and less than the diameter of a medullary canal for which the tip is configured. The diameter of the tip may be the same as, or less than, the diameter of the shaft. In some examples, the diameter of the tip is less than about one-half or one-fourth the diameter of the shaft. In some examples, the length of the tip is at least about five times or ten times the diameter of the tip. The diameter of the tip may be generally constant or may vary along the length, for example, tapering toward the distal end of the tip. Exemplary tip diameters include, but are not limited to, about 0.5-3 mm, among others.

The tip may be flexible or rigid. Flexible, as used in the context of the tip, refers generally to an ability to be bent significantly in response to engagement with bone as the reamer is being pushed along the medullary canal. The tip is generally configured to bend reversibly, so that the tip returns to its original shape after the tip moves out of engagement with bone. Reversible bending may allow the reamer to be used more than once, for example, as the reamer is moved backwards and forwards in the same bone, and/or from bone to bone. Bending of the tip may guide the cutting head to follow a nonlinear path along a medullary canal, so that bone is not removed and/or damaged unnecessarily. The tip is bent significantly, as used herein, if the tip deviates from a linear configuration by at least about one, two, or five degrees, among others, during typical reaming procedures. Although flexible, the tip may be configured to be more rigid than guide wires used with wire-guided reamers, to facilitate the tip moving and/or holding bone fragments, before, during, and/or after fracture reduction. In some embodiments, the tip may be configured to be rigid, so that the tip does not flex significantly during a typical reaming procedure. A rigid tip may be particularly suitable for reaming a linear path along a medullary canal.

I.E Compositions

The reamer may be made of any suitable biocompatible material. For example, the reamer may be made of a biocompatible metal such as stainless steel, a titanium alloy, a nickel-titanium alloy, and/or a cobalt-chromium alloy, among others. Alternatively, or in addition, the reamer may be formed, at least partially, of a ceramic, a plastic, and/or a polymer, among others. The reamer may have a generally uniform composition, or components of the reamer may have different compositions, such as when the components are formed separately from different materials. In some examples, one or more components of the reamer may vary in composition within the component, due, for example, to a surface coating (such as a surface coating that facilitates formation of a cutting edge on the cutting head).

II. Methods of Making Reamers

Reamers in accordance with the present teachings may be fabricated by any suitable method(s). For example, the reamers may be machined, cast, molded, and/or the like. The reamers may be formed unitarily or may be formed by assembly of two or more separate components. Each component of a reamer may be secured fixedly and/or adjustably to adjacent structures of the reamer.

The shaft may be formed, in some examples, unitarily with the tip. The cutting head thus may be formed unitarily along with the shaft and tip or may be a separate component assembled with the shaft-tip component. In some embodiments, the cutting head may include a through-hole through which the shaft-tip component may be received. The cutting head then may be positioned suitably along the shaft-tip component and then secured to this component, such as by welding, with an adhesive, crimping/deforming the cutting head, a lock screw, and/or the like.

The cutting head may be a module, in some examples, that is assembled with the shaft. For example, the cutting head may be configured to be threaded onto the shaft. The tip may be formed unitarily with the cutting head or may be a separate component that is secured to the cutting head. In any case, reamers with different cutting heads may be assembled using the same shaft.

The tip may be a module, in some examples, that is assembled with the shaft. For example, the tip may be threaded into the cutting head or secured otherwise. In any case, reamers with different tips (for example, tips of different lengths, diameters, flexibilities, etc.) may be assembled with the same cutting head and/or shaft.

III. Methods of Using Reamers

The present teachings provide methods of reaming bones to widen cavities in the bones and methods of fixing the bones. The methods may include any suitable combination of the following steps, performed any suitable number of times and in any suitable order. Exemplary configurations that may be produced by performing the method steps are illustrated in FIGS. 2-7.

III.A Selecting a Bone

The methods may include selecting a bone to be reamed and/or fixed. The bone may include any suitable bone, selected for any suitable purpose, such as repair, generally from a patient being treated. Exemplary bones are long bones, such as bones of the arms (humerus, radius, ulna), legs (femur, tibia, fibula), clavicles, metatarsals, or metacarpals, among others. In some embodiments, the methods may ream the medullary canal of an ulna or a tibia. The selected bone may include a discontinuity, such as a fracture, a cut created surgically, a nonunion, a malunion, and/or a developmental defect, among others. Alternatively, or in addition, the bone may be structurally unsound for another reason.

Figure 2:
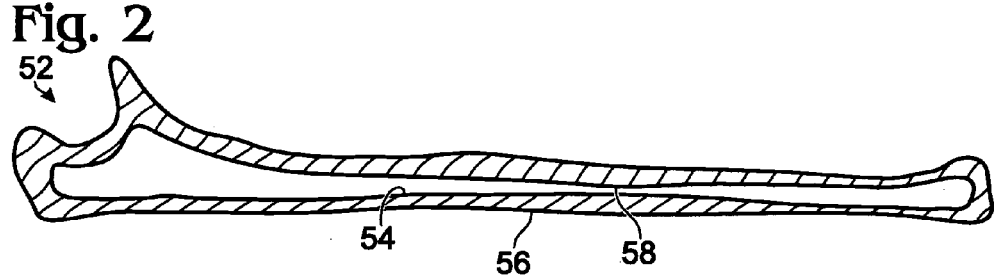
FIG. 2 is a longitudinal sectional view of an exemplary bone, an ulna, that may be reamed, in accordance with aspects of the present teachings.
Figure 3:
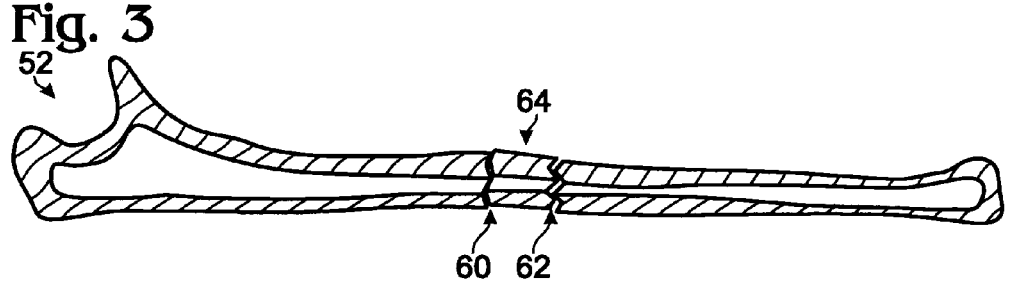
FIG. 3 is a view of the ulna of FIG. 2 in an exemplary fractured condition in which the ulna may be reamed and/or fixed by performing steps of an exemplary method for reaming and/or fixing bones, in accordance with aspects of the present teachings.

FIGS. 2 and 3 show an exemplary bone, an ulna 52, which may be selected for reaming. Ulna 52 includes a medullary canal 54 that extends along the long axis of this bone. The medullary canal narrows in a central region of the ulna's shaft 56 to form an isthmus 58 that may be reamed. In FIG. 2, ulna 52 is intact, and in FIG. 3, the ulna has been fractured at fractures 60, 62 disposed in fractured region 64. The position, number, and/or severity of the fractures may determine if internal fixation with a fixation device placed in the bone's medullary canal is suitable.

III.B Forming an Entry Hole in the Selected Bone

The methods also may including forming an entry hole in the selected bone. The entry hole may mark and/or provide an entry location for a reamer and a fixation device. The entry hole may be sized to receive the reamer, and thus may have a diameter greater than the diameter of the cutting head of the reamer. Alternatively, the entry hole may be of smaller diameter, so that the reamer enlarges the entry hole with its cutting head so that the reamer and/or a fixation device can travel through the entry hole. The entry hole may be formed at any suitable position in the bone. For example, the entry hole may be formed at an end of a bone, generally aligned with the medullary canal of the bone. The entry hole may be formed by any suitable approach, such as drilling or punching, or by sawing off the end of the bone, among others. In some cases, the bone may be fractured and/or otherwise breached such that a reamer and/or fixation device may be positioned, through the fracture or breach, without forming an additional entry hole.

Figure 4:
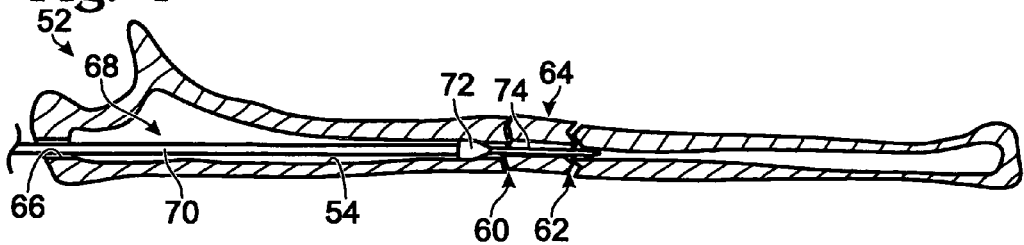
FIG. 4 is a view of the fractured ulna of FIG. 3, with an exemplary bone reamer received in the medullary canal of the ulna from a proximal opening in the ulna and with a tip portion of the reamer spanning a fracture in the bone, in accordance with aspects of the present teachings.

FIG. 4 shows ulna 52 with an entry hole 66 formed in a proximal end of the ulna. Alternatively, the entry hole may be formed in a distal end of the ulna, particularly when the fracture is disposed closer to the distal end. Accordingly, in some examples, one of the opposing ends of the bone (the end at which the entry hole is formed) may be selected for being closer to the fracture(s) relative to the other opposing end.

III.C. Selecting a Reamer

The methods also may include selecting a reamer. The reamer may have any of the features described above in Section I and elsewhere in the present teachings. The reamer may have a length greater than the depth to which the reamer is to be placed in the bone. The reamer also may have a diameter of cutting head corresponding to the diameter of the reamed cavity to be formed. In some examples, the diameter of cutting head may be selected to correspond substantially to a diameter of fixation device (such as a rod) to be placed into the reamed cavity. In some examples, the diameter of the cutting head may be selected to increase the diameter of a previously reamed cavity, for example, when sequentially using a series of reamers with progressively larger cutting heads to progressively widen the cavity. In some examples, the diameter of the cutting head used may depend on the diameter of the bone shaft and/or medullary canal being reamed, which may be influenced at least in part by the type/density of selected bone, and/or the age, sex, and/or general health of the patient, among other factors.

III.D. Placing a Reamer, and Reaming a Bone

The reamer may be placed along the medullary canal of the bone, to widen the medullary canal. The reamer may enter the medullary canal through the entry hole. The reamer may be rotated or pivoted as it travels along the medullary canal, so that the cutting head cuts bone from the wall of the medullary canal. The reamer may travel along any suitable portion of the medullary canal, but generally past the isthmus of the medullary canal. In some embodiments, the reamer may be placed along a nonlinear path in the bone, so that the tip and/or shaft of the reamer bends as it travels along this nonlinear path.

The reamer may have a tip that guides the cutting head of the reamer along the medullary canal, through and past a fracture region and/or isthmus. The tip may be flexible enough to bend somewhat when the tip engages intact regions of the medullary canal, and stiff enough to resist bending when the tip engages bone fragments disposed in fractured regions of the medullary canal. The tip thus may facilitate finding and/or forming a path through a fractured region for the cutting head.

The fracture may be reduced, in some examples, at least partially with the tip disposed in a fractured region of the bone. The tip thus may help to hold bone fragments in a reduced configuration in preparation for action of the cutting head in the fractured region. For example, a surgeon may reduce the fracture and/or reposition bone fragments, at least partially, with the tip spanning a fracture of the fractured bone region. The surgeon may observe segment alignment directly, indirectly based on the shape of overlying soft tissue, and/or with a suitable instrument (such as with a fluoroscope). In some examples, the instrument may be configured to detect bone and the tip and/or other portions of the reamer, so that the relative disposition of the reamer and bone may be determined.

Figure 5:
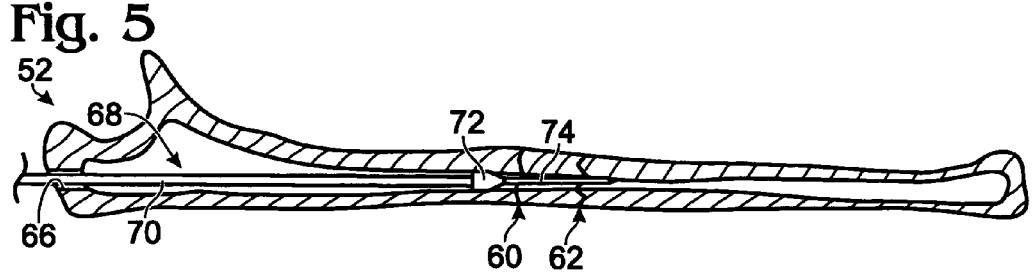
FIG. 5 is a view of the fractured ulna and bone reamer of FIG. 4 after reduction of the fracture while the tip portion spans the fracture, in accordance with aspects of the present teachings.

FIGS. 4 and 5 show a reamer 68 disposed in medullary canal 54 of ulna 52. The reamer may have a shaft 70 extending through entry hole 66. The reamer also may have a cutting head 72 secured to the shaft, and a guide tip 74 secured to the cutting and extending distally from the cutting head. FIG. 4 shows tip 74 spanning fractures 60 and 62 before adjusting the reduction of these fracture. FIG. 5 shows the reamer at the same depth of insertion into bone as in FIG. 4, and after reduction of fractures 60 and 62 has been adjusted, to improve alignment of bone fragments. Tip 74 thus may help to hold fractured bone fragments in place during and/or after their re-positioning, and/or as the cutting head is advanced.

Figure 6:
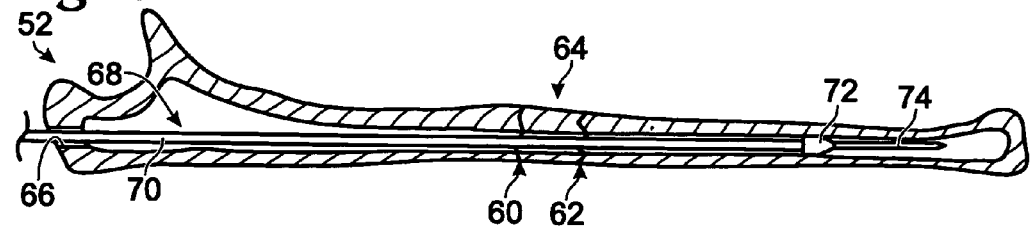
FIG. 6 is a view of the fractured ulna and bone reamer of FIG. 4 after the reamer has widened the isthmus of the medullary canal by advancement of a cutting head of the reamer past the fracture and the isthmus, in accordance with aspects of the present teachings.

FIG. 6 shows ulna 52 with cutting head 72 of reamer 68 advanced past the isthmus of the ulna. At this position of reamer advancement, reaming may be complete, with the minimum diameter of the medullary canal in the bone shaft defined by action of the reamer. Accordingly, further advancement of the reamer along the canal may be unnecessary and potentially harmful to bone. Reaming thus may be monitored for completion by manually measuring the depth of reamer insertion, by observing a depth gauge on the reamer, by noting a change in resistance of the reamer to advancement, by using a fluoroscope or other suitable reamer/bone detection instrument, and/or by engagement of a stop structure on the reamer with bone adjacent the entry hole, among others. Suitable reaming depth also may be determined using an x-ray template and/or other mechanism for determining dimensions based on an x-ray of the bone.

III.E. Securing a Bone

The reamer may be removed from the medullary canal after a suitable amount of reaming has been performed. After removal, a fixation device, such as an intramedullary rod (also termed a nail) and/or a stem of a prosthesis may be placed into the reamed medullary canal and secured to bone with suitable fasteners (such as bone screws, wires, pins, an adhesive, etc.). A rod/nail/prosthesis stem may be linear or nonlinear. In some examples, the rod and/or nail may be flexible so that it can bend according to shape of the medullary canal. In some examples, the fixation device may be disposed completely in the bone, so that none of the fixation device protrudes above the bone surface. In some examples, a portion of the fixation device may be disposed exterior to the bone, for example, to provide a portion of a prosthesis that replaces an articulating portion and/or an end of the bone. Alternatively, before introduction of a fixation device, the medullary canal may be reamed additionally with one or more other reamers, generally reamers with cutting heads of increased diameter.

Figure 7:
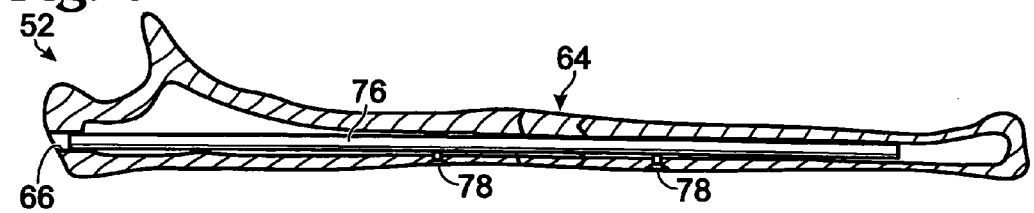
FIG. 7 is a view of the fractured ulna of FIG. 6 after removal of the reamer and fixation of the ulna with an intramedullary rod received in the widened medullary canal and secured to the ulna on opposing sides of the fracture, in accordance with aspects of the present teachings.

FIG. 7 shows ulna 52 fixed with an intramedullary rod 76 after the reamer has been removed from the bone. Rod 76 may span fractured region 64 and may be secured to opposing sides of the fractured region with fasteners, such as bone screws 78. The rod may be configured to substantially fill entry hole 66, or the entry hole may be plugged with a plug placed over the end of the rod, among others.

IV. Kits

The bone reamers of the present teachings may be sold individually or as components of a kit. The kit may include one or more reamers, and optionally a fixation device(s) (such as a rod or prosthesis, among others) with a diameter corresponding substantially to the diameter of the cutting head of at least one of the reamers. The kit also or alternatively may include a driver to drive the reamer (and/or bone screws); fasteners for use with the fixation device to secure the fixation device to bone; an x-ray template; a depth gauge; a stop structure to restrict advancement of the reamer; instructions for use of the kit; a drill, punch, and/or saw for forming an entry hole; and/or the like.

The kit may include two or reamers. The reamers may have distinct cutting heads. The cutting heads may differ according to size (diameter, length, etc.), shape (overall shape and/or cutting flute number/depth, etc.), and/or the like. Alternatively, or in addition, the reamers may have distinct shafts and/or tips (different lengths, diameters, shapes, etc.). In some embodiments, the reamers may include a progressive set of reamers for sequential use in widening the medullary canal of a bone. This progressive set may have cutting heads with diameters that increase progressively, in constant or varying increments.

V. Example

This example describes selected aspects of the present teachings, including an exemplary reamer (see FIGS. 8A-C) and exemplary methods of constructing and using the exemplary reamer. This example is included for illustration and is not intended to limit or define the entire scope of the present teachings.

Figure 8A:
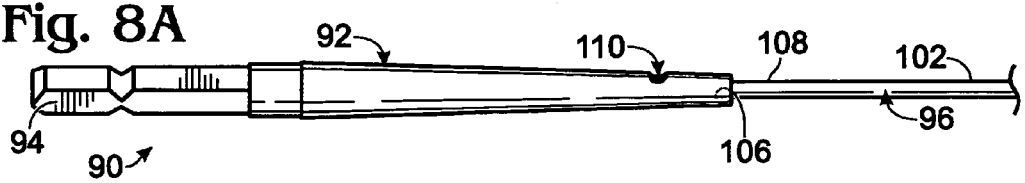
FIGS. 8A-C are fragmentary views of proximal, intermediate, and distal regions, respectively, of another exemplary reamer, in accordance with aspects of the present teachings.
Figure 8B:
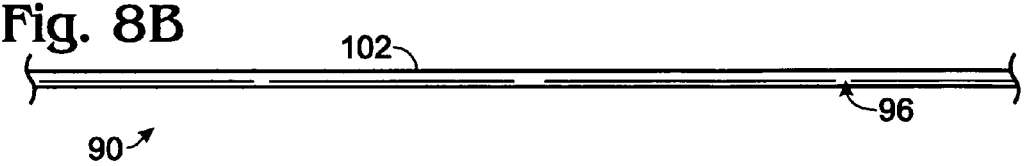
Figure 8C:
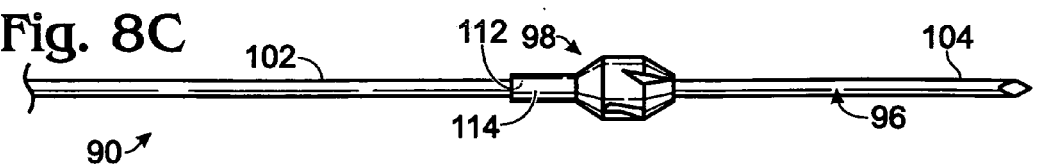

FIGS. 8A-8C show proximal, intermediate, and distal regions, respectively, of an exemplary reamer 90. Reamer 90 may include a base component 92 having a driver-engagement structure 94 configured to be received by a driver. Reamer 90 also may include a rod component 96 and a cutting head 98 received on the rod component. The rod component 96 may form a shaft 102 and a tip 104 of the reamer. In some examples, the rod component may have a unitary construction, so that the shaft and the tip are formed unitarily. The shaft and the tip thus may have the same or different diameters, based on whether the rod component has a constant or varying diameter. In some embodiments, the rod component may taper toward the tip.

Reamer 90 may be constructed by assembling the base component, the shaft component, and the cutting head so that they are secured to one another. For example, base component 92 may define a socket 106 into which a proximal end 108 of the shaft component may be inserted. The shaft component may be threaded, so that this component can be threadably engaged with the base component. Alternatively, these two components may be secured to one another by welding, riveting, a lockscrew, and/or the like. In some embodiments, these two components may be secured to each other by crimping the base component against the rod component (particularly so that a crimped region of the base component enters a recess defined by the rod component), shown at 110. The cutting head may define a through-hole 112 sized to receive the rod component. The cutting head thus may be placed on the rod component at any suitable axial position along the rod component to create a tip of a suitable length. The cutting head then may be secured to the rod component by any suitable approach, such as any of the approaches described above for securing the base component to the rod component. In some examples, the cutting head may include a neck region 114 that may be crimped against the rod component, or which may be secured otherwise to the rod component.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. A system for fixing a bone, comprising:
   a reamer including (i) a shaft portion having a proximal end and a distal end and defining a longitudinal axis, the shaft portion being flexible and at least substantially noncannulated, (ii) a cutting head disposed adjacent the distal end of the shaft portion, and (iii) an elongate, flexible tip portion in fixed axial relation to the cutting head and extending distally from the cutting head in opposing relation to the shaft portion, wherein the tip portion and the cutting head each have a length measured parallel to the longitudinal axis, wherein the length of the tip portion is greater than the length of the cutting head, wherein the cutting head includes a tapered section disposed adjacent the tip portion and forming a leading face that decreases in diameter as the leading face extends to the tip portion, and wherein the leading face includes at least one flute forming a cutting edge on the leading face, thereby endowing the cutting head with end-cutting ability; and
   an intramedullary nail to fix the bone,
   wherein the intramedullary nail has a longitudinal midpoint that conceptually divides the nail into a leading half and a trailing half, wherein the leading half is adapted to enter the bone before the trailing half, and wherein the trailing half has a substantially constant diameter that corresponds to a diameter of the cutting head.

2. The system of claim 1, wherein the tip portion includes a flexible body and a tapered end disposed distally of the flexible body.

3. The system of claim 1, wherein the cutting head is at least substantially solid.

4. The system of claim 1, wherein the cutting head includes a relatively cylindrical body and a relatively conical nose projecting from the body toward the tip portion, and wherein the nose forms the leading face.

5. The system of claim 1, wherein the tip portion includes opposing leading and trailing ends and also includes a diameter that remains at least substantially constant as the tip portion extends along the longitudinal axis between the leading and trailing ends.

6. The system of claim 1, wherein the tip portion and the cutting head each have a length measured parallel to the longitudinal axis, and wherein the length of the tip portion is at least about twice the length of the cutting head.

7. The system of claim 1, wherein the cutting head has a diameter, and wherein the length of the tip portion is at least about twice the diameter of the cutting head.

8. The system of claim 1, wherein the cutting head and the shaft portion each have a diameter, and wherein the diameter of the cutting head is at least about twice the diameter of the shaft portion.

9. The system of claim 1, wherein the shaft portion and the tip portion each have a diameter, and wherein the diameter of the shaft portion is greater than the diameter of the tip portion.

10. The system of claim 1, wherein the tip portion tapers distally to a point.

* * * * *